US012478745B2

(12) United States Patent
Gawell

(10) Patent No.: US 12,478,745 B2
(45) Date of Patent: Nov. 25, 2025

(54) HOUSING FOR A MEDICAMENT DELIVERY DEVICE

(71) Applicant: SHL MEDICAL AG, Zug (CH)

(72) Inventor: Elin Gawell, Johanneshov (SE)

(73) Assignee: SHL Medical AG, Zug (CH)

( * ) Notice: Subject to any disclaimer, the term of this patent is extended or adjusted under 35 U.S.C. 154(b) by 866 days.

(21) Appl. No.: 17/774,268

(22) PCT Filed: Oct. 14, 2020

(86) PCT No.: PCT/EP2020/078920

§ 371 (c)(1),
(2) Date: May 4, 2022

(87) PCT Pub. No.: WO2021/094051

PCT Pub. Date: May 20, 2021

(65) Prior Publication Data

US 2022/0387732 A1 Dec. 8, 2022

(30) Foreign Application Priority Data

Nov. 15, 2019 (EP) .................................... 19209325

(51) Int. Cl.
*A61M 5/32* (2006.01)

(52) U.S. Cl.
CPC ........ *A61M 5/3271* (2013.01); *A61M 5/3202* (2013.01)

(58) Field of Classification Search
CPC .. A61M 5/326; A61M 5/3202; A61M 5/3271; A61M 2005/2026;
(Continued)

(56) References Cited

U.S. PATENT DOCUMENTS 4,681,567 A 7/1987 Masters et al.
4,702,738 A 10/1987 Spencer
(Continued)

FOREIGN PATENT DOCUMENTS

EP 2624882 B1 4/2021
WO 2012045350 A1 4/2012
WO 2012096620 A1 7/2012

OTHER PUBLICATIONS

International Search Report and Written Opinion for Int. App. No. PCT/EP2020/078920, mailed Nov. 16, 2020.

*Primary Examiner* — Laura A Bouchelle
(74) *Attorney, Agent, or Firm* — McDonnell Boehnen Hulbert & Berghoff LLP

(57) ABSTRACT

A housing for a medicament delivery device is presented having a shell extending along an axis in an axial direction from a proximal end to a distal end, and a medicament delivery member guard moveably attached to the shell. The medicament delivery member guard extends in the axial direction from a proximal end to a distal end. The shell has a slit extending in the axial direction and the medicament delivery member guard has a protrusion extending in the axial direction, and/or the medicament delivery member guard has a slit extending in the axial direction and the shell has a protrusion extending in the axial direction. The medicament delivery member guard is configured to move in the axial direction from a first axial position relative to the shell (12) to a second axial position relative to the shell.

13 Claims, 2 Drawing Sheets

(58) Field of Classification Search
CPC .. A61M 2005/2073; A61M 2005/3247; A61M 2005/3267
See application file for complete search history.

(56) References Cited

U.S. PATENT DOCUMENTS

| | | | | |
|---|---|---|---|---|
| 4,923,445 | A | 5/1990 | Ryan | |
| 5,290,255 | A | 3/1994 | Vallelunga et al. | |
| 5,591,138 | A * | 1/1997 | Vaillancourt ....... | A61M 5/3271 604/263 |
| 7,001,364 | B1 * | 2/2006 | Farhi .................. | A61M 5/3272 604/110 |
| 8,801,674 | B2 * | 8/2014 | Rolfe .................. | A61M 5/2033 604/218 |
| 2003/0078546 | A1 | 4/2003 | Jensen | |
| 2019/0046735 | A1 | 2/2019 | Ingerslev et al. | |

* cited by examiner 10
12
14
16
18
20
21
22
24
30
A
A

HOUSING FOR A MEDICAMENT DELIVERY DEVICE

CROSS REFERENCE TO RELATED APPLICATIONS

The present application is a U.S. National Phase application pursuant to 35 U.S.C. § 371 of International Application No. PCT/EP2020/078920 filed Oct. 14, 2020, which claims priority to European Patent Application No. 19209325.0 filed Nov. 15, 2019. The entire disclosure contents of these applications are herewith incorporated by reference into the present application.

TECHNICAL AREA

The disclosure concerns a housing for medicament delivery devices, and particularly a housing comprising a shell and a medicament delivery member guard.

BACKGROUND

Some auto-injectors have a needle guard that can only be retracted once and is locked automatically after use. Although this is a useful safety feature, it also has the drawback that users can retract the needle guard prior to use, for example by pressing the edges of the needle guard with their fingers to see how it works, with the result that the needle guard is locked and the auto-injector can no longer be used.

SUMMARY

The present disclosure is defined in the appended claims, to which reference should now be made.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the term "longitudinal", "longitudinally", "axially" or "axial" refer to a direction extending from the proximal end to the distal end, typically along the device or components thereof in the direction of the longest extension of the device and/or component.

Similarly, the terms "transverse", "transversal", "transversally" refer to a direction generally perpendicular to the longitudinal direction.

A first aspect of the present disclosure concerns a housing for a medicament delivery device, the housing comprising a shell extending along an axis in an axial direction from a proximal end to a distal end, and a medicament delivery member guard moveably attached to the shell, the medicament delivery member guard extending in the axial direction from a proximal end to a distal end; the shell comprising a slit extending in the axial direction and the medicament delivery member guard comprising a protrusion extending in the axial direction, and/or the medicament delivery member guard comprising a slit extending in the axial direction and the shell comprising a protrusion extending in the axial direction; wherein the medicament delivery member guard is configured to move in the axial direction from a first axial position relative to the shell to a second axial position relative to the shell, such that in the first axial position the medicament delivery member guard is rotatable around the axis relative to the shell from a locked position in which the protrusion cannot enter the slit to an unlocked position in which the protrusion can enter the slit, and such that in the second axial position rotation of the medicament delivery member guard around the axis relative to the shell is limited, and the protrusion is in the slit.

A number of potential advantages may result from this new housing. It can provide a device that can be locked and unlocked by the user, by incorporation of the housing into single or multi-use medicament delivery devices. The present disclosure can be incorporated into both manual injection and auto-injection medicament delivery devices. It can avoid accidental locking of the needle guard by the user. If the user accidentally (or experimentally) retracts the needle guard without activating injection, they can recover that error and the device can still be used. It can therefore reduce the number of devices that are not used because the needle guard was accidentally locked by the user prior to injection. The protrusions can also help the user grip the needle guard to rotate the needle guard to lock/unlock the needle guard.

In one embodiment, the shell comprises a slit extending in the axial direction and the medicament delivery member guard comprises a protrusion extending in the axial direction. In one embodiment, the protrusion extends from the medicament delivery member guard away from the axis in a radial direction.

In one embodiment, the slit extends through the shell in a radial direction relative to the axis. In one embodiment, the slit extends only part of the way through the shell in a radial direction relative to the axis. In one embodiment, the shell comprises an inner surface facing towards the axis, and the slit is in the inner surface of the shell. In one embodiment, the slit extends in the axial direction from the proximal end of the shell.

In one embodiment, the protrusion extends from the proximal end of the medicament delivery member guard. In one embodiment, the medicament delivery member guard is inside the shell. In one embodiment, the protrusion and the slit are adjacent to one another in the axial direction when the medicament delivery member guard is in the first axial position. In one embodiment, the protrusion and the slit are spaced apart from one another in the axial direction when the medicament delivery member guard is in the first axial position. In one embodiment, the medicament delivery member guard comprises a slit extending in the axial direction and the shell comprises a protrusion extending in the axial direction.

A second aspect of the present disclosure concerns a medicament delivery device comprising the housing described above. In one embodiment, the medicament delivery device is an auto-injector. In one embodiment, the medicament delivery device, for example an auto-injector, comprises a cap, the cap comprising a lock to stop the protrusion from entering the slit while the cap is on the medicament delivery device.

A third aspect of the present disclosure concerns a housing for a medicament delivery device, the housing comprising a shell extending in an axial direction from a proximal end to a distal end, the shell comprising a slit extending in the axial direction; a medicament delivery member guard moveably attached to the shell, the medicament delivery member guard extending in the axial direction from a proximal end to a distal end, and the medicament delivery member guard comprising a protrusion extending in the axial direction; wherein the medicament delivery member guard is configured to move in the axial direction from a first axial position relative to the shell to a second axial position relative to the shell, wherein the medicament delivery member guard is rotatable around the axis relative to the shell when in the first axial position and wherein the protrusion is in the slit when the medicament delivery member guard is in the second axial position, such that rotation of the medicament delivery member guard around the axis relative to the shell is limited in the second axial position.

A fourth aspect of the present disclosure concerns a housing for a medicament delivery device, the housing comprising a shell with a longitudinal axis, the shell extending in an axial direction from a proximal end to a distal end and in a circumferential direction around the axis, the shell comprising a slit extending in the axial direction; a medicament delivery member guard moveably attached to the shell, the medicament delivery member guard extending in the axial direction from a proximal end to a distal end, and the medicament delivery member guard comprising a protrusion extending in the axial direction; wherein the medicament delivery member guard is moveably attached to the shell such that during use the medicament delivery member guard can move relative to the shell from a first circumferential position to a second circumferential position, wherein in the first circumferential position, the protrusion cannot enter the slit, and wherein in the second circumferential position, the protrusion can enter the slit.

BRIEF DESCRIPTION OF THE DRAWINGS

Embodiments of the present disclosure will now be described by way of example only and with reference to the accompanying drawings, in which.

DETAILED DESCRIPTION

Figures 1, 2, 3, 4:
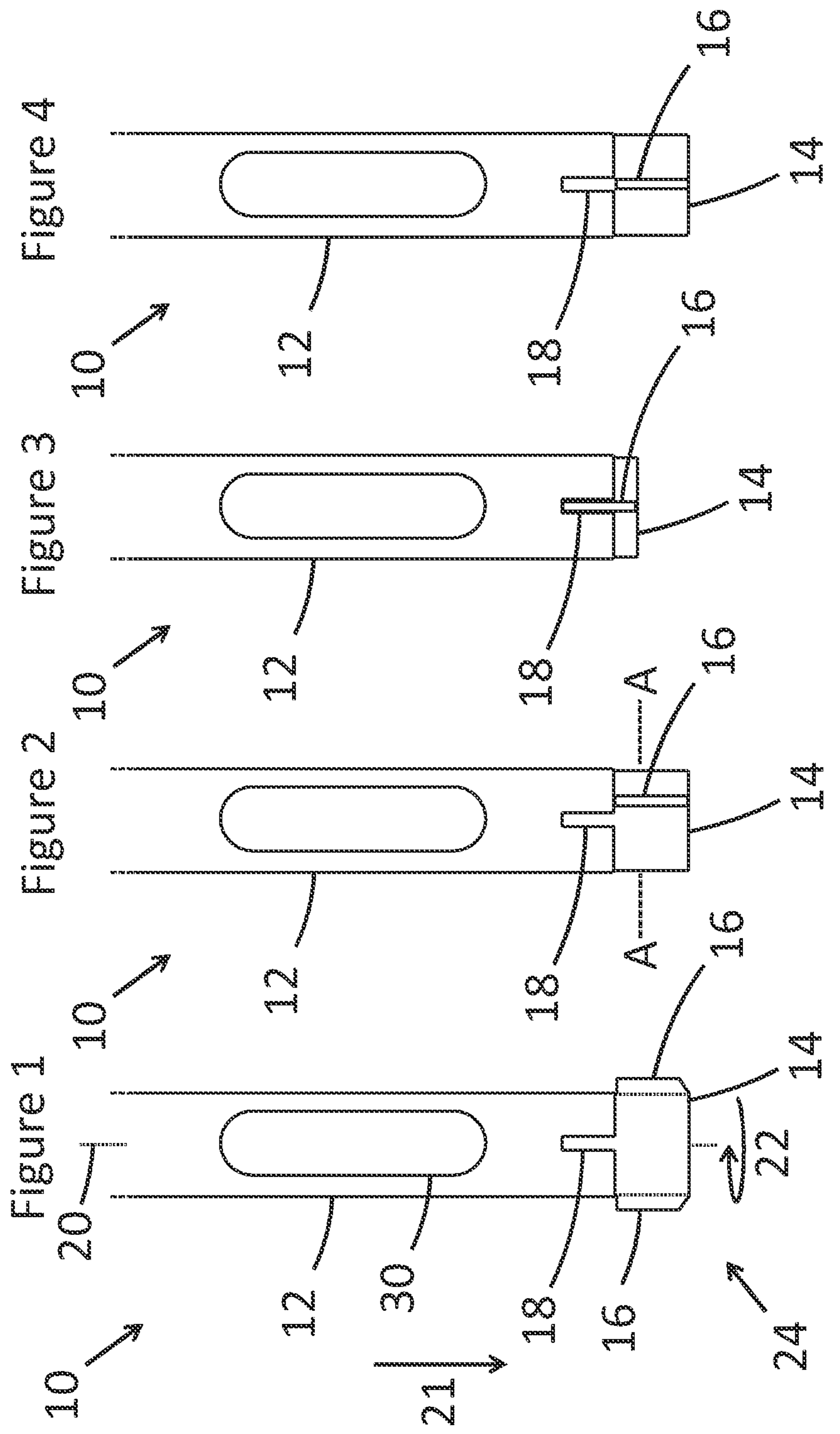
FIGS. 1 to 4 show side views of a housing of a medicament delivery device in various positions.
Figure 5:
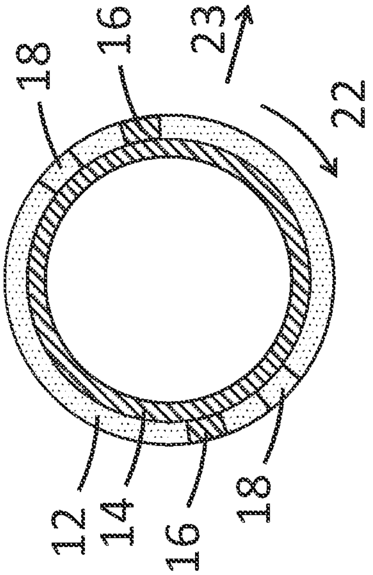
FIG. 5 shows a view in the distal direction from the cross-section at line A-A of FIG. 2.

FIGS. 1 to 5 show a housing 10 of a medicament delivery device, the housing 10 comprising a shell 12 and a needle guard 14. The shell and the needle guard extend in an axial direction 21 relative to a longitudinal axis 20 from a proximal end 24 to a distal end (not shown). The needle guard 14 is moveably attached to the shell 12. The shell 12 comprises two slits 18 extending in the axial direction 21 (see also FIG. 5), and the needle guard 14 comprises two corresponding protrusions 16 extending in the axial direction 21. As such, the needle guard 14 is configured to move in the axial direction 21 from a first axial position (e.g. FIGS. 1, 2, 4) relative to the shell 12 to a second axial position (e.g. FIG. 3) relative to the shell 12, such that in the first axial position the needle guard 14 is rotatable around the axis 20 relative to the shell 12 from a locked position in which the protrusions 16 cannot enter the slits 18 to an unlocked position in which the protrusions 16 can enter the slits 18, and such that in the second axial position rotation of the needle guard 14 around the axis 20 relative to the shell 12 is limited, and the protrusions 16 are in the slits 18. An optional window 30 is also provided in the shell 12.

After assembly, the medicament delivery device would typically be provided with the slit (or slits) and protrusion (or protrusions) spaced apart in the circumferential direction 22. Prior to use, the user would first remove a cap from the device if the device has a cap. The user would then rotate the guard relative to the shell so that the slit and the corresponding protrusion align. The device can now be used to deliver a medicament. Alternatively, the user can also change their mind at this point, and can rotate the guard relative to the shell again so that the protrusion and the slit no longer align, which can make the device safe again and allow the user to leave the device to use later.

With the protrusion and the slit aligned, the user can push the guard against the injection site to retract the guard, and the protrusion will enter the slit as the guard retracts (see FIG. 3, for example). In embodiments where the device is activated by retraction of the guard, injection would then be activated. In embodiments with an activation button that needs pushing (either before or after retraction of the guard), the activation button would typically also need to be pushed to allow the injection to commence.

Once the injection is complete, the user then removes the device from the injection site, and the guard will typically automatically extend back out again, for example as a result of a resilient member such as a spring between the shell and the guard. The user can then rotate the guard relative to the shell to move the protrusion and slit out of alignment, once again stopping the guard from moving axially. The device can then be disposed of, or alternatively can be used again in the case of multi-use devices, typically after removal of the used needle and addition of a new needle and/or removal of the used medicament cartridge and addition of a medicament cartridge.

A medicament delivery device may be provided comprising the housing. The medicament delivery device may be an auto-injector or a pen injector, for example. In one example, the medicament delivery device comprises a powerpack, a medicament container inside the shell, and a cap, wherein the medicament container comprises a medicament barrel, a medicament delivery member such as a needle and a medicament delivery member shield, and wherein the cap comprises a needle shield remover. The medicament delivery device may be single use or multiple use.

As described herein, the protrusion is generally on the medicament delivery member guard and the slit is generally on the shell. However, the positions of the slit and the medicament delivery member guard can be switched in some embodiments, with the slit on the medicament delivery member guard and the protrusion on the shell. In some embodiments, the shell comprises a slit extending in the axial direction and the medicament delivery member guard comprises a protrusion extending in the axial direction, and the medicament delivery member guard comprises a slit extending in the axial direction and the shell comprises a protrusion extending in the axial direction.

One particular shape for the housing, shell and needle guard is shown in the Figures, but other shapes are possible. The shell 12 is typically tubular. The shell 12 may be the outer shell of a medicament delivery device, although in some embodiments it is not the outermost component of the housing and/or of the device. In some embodiments, such as the embodiment shown in the Figures, the medicament delivery member guard is inside the shell. However, the needle guard may alternatively be outside the shell, particularly in embodiments that include a further outer housing outside of the housing 10. An outer housing outside the housing described herein can be included to provide an ergonomically shaped exterior for the device, which can improve user experience. Where a needle guard is described herein, this can also be generalised to a medicament delivery member guard. The medicament delivery member guard typically surrounds a medicament delivery member such as a needle. The medicament delivery member guard is typically a tubular body. The medicament delivery member guard typically mirrors the shape of the shell.

The example in the Figures has two protrusions 16. Alternatively, one, three or more protrusions may be provided. When more than one protrusion is provided, the protrusions would typically be spaced out equally in the circumferential direction 22, although irregular spacing could also be used. The number of slits may be the same as the number of protrusions; alternatively, there could be more slits than protrusions.

The example in the Figures shows the protrusions as extending from the proximal end of the needle guard to a position adjacent to the shell in the axial direction. However, some or all of the protrusions could be spaced apart from the shell in the axial direction. Some or all of the protrusions could alternatively or additionally be spaced apart in the axial direction from the proximal end of the needle guard.

The example in the Figures shows the protrusions as extending further in the axial direction than the slit (this is most clearly apparent in FIG. 3). However, the protrusions could be the same length as the slit in the axial direction, or the slit could be longer than the protrusion in the axial direction.

The protrusions may be ribs, as shown in the Figures, with a rectangular cross-section when looked at from perpendicular to the axis (so from the side view in FIGS. 1 to 4), or one or more of the ribs may have another shape, such as a circular cross-section when looked at from perpendicular to the axis.

The protrusions are shown with the same width from their proximal end to their distal end, but one or more of the protrusions could also vary in width at different positions in the axial direction. Similarly, the slits are shown with the same width from their proximal end to their distal end, but one or more of the slits could also vary in width. For example, a slit could be wider at the proximal end to make it easier for the user to line up the protrusion with the slit. For example, a slit could be tapered from the proximal end towards the distal end, with the width in the circumferential direction being greater at the proximal end.

As with the protrusions 16, various modifications are possible with the slits 18. Instead of two slits, one, three or more slits may be provided. The spacing of the slits in the circumferential direction would typically match that of the protrusions. The slit or slits may be the same width or wider than the corresponding protrusion or protrusions that are intended to enter the slit or slits. When more than one slit is provided, the slits would typically be the same width in the circumferential direction, but widths may alternatively vary.

Where two or more protrusions (and corresponding slits) are provided, the device can be designed so that any slit can enter any protrusion, or can be designed (for example by differing slit widths and protrusion widths or by irregular spacing of the slits and correspondingly of the protrusions) so that there is a limited number of rotational positions (for example only one rotational position) at which the protrusions can enter the slits (i.e. no rotational symmetry). For example, two protrusions could be provided at 90 degrees apart in the circumferential direction (rather than the 180 degrees shown in the example in the Figures), with the two corresponding slits also 90 degrees apart in the circumferential direction.

The slits may fully extend through the shell in the radial direction 23, or one or more of the slits may only extend part of the way through the shell in the radial direction, in which cases the slit may be formed by a recess or notch in the surface of the shell. The slit typically extends from the proximal end of the shell, depending on the shape of the shell.

In terms of the position relative to each other, the first axial position and the second axial position are different positions in the axial direction 21. In the first axial position the proximal end of the needle guard 14 is normally further from the proximal end of the shell 12 when compared to the second axial position. The first axial position may be the axial position where the proximal end of the needle guard 14 is furthest from the proximal end of the shell 12. Both the first axial position and the second axial position may be a specific axial position, or may encompass a range of axial positions, in which case the range of axial positions encompassed by the second axial position would typically be larger. In more detail, the freedom of movement of the needle guard relative to the shell can be split into three states. In the first state, the needle guard can rotate relative to the shell but is limited in movement in the axial direction. Examples of this first state (locked position) are shown in FIGS. 1 and 2. In the second state (unlocked position), the needle guard can rotate and also move in the axial direction, and an example of this state is shown in FIG. 4. In the third state, the needle guard can move in the axial direction, but has limited rotation, and an example of this state is shown in FIG. 3. The first and second states together could be considered to correspond to the first axial position and the third state could be considered to correspond to the second axial position.

The freedom to rotate in the first axial position could be a complete freedom to rotate 360 degrees, or could be somewhat limited, for example to 90 degrees. The freedom to move in the axial direction in the first axial position could be completely restricted, or a small amount of axial movement could be permitted, for example in embodiments where the slit is spaced apart from the protrusion in the axial direction when in the first position. In the second axial position, rotation can be completely stopped or can be limited but still allow some rotation (e.g. up to 10 degrees), for example in embodiments where the slits are wider than the protrusions in the circumferential direction. This may improve usability by making it easier to line up the protrusion with the slit.

In the example shown in the Figures, the medicament delivery member guard could be allowed to rotate freely relative to the shell in the first axial position, or the surfaces of the medicament delivery member guard and/or of the shell could be contoured such that rotation preferentially or naturally stops in specific positions. This could assist the user in lining up the slit and the protrusion (and/or in de-aligning the slit and the protrusion, for example after injection).

In embodiments with a medicament container comprising a cap, the cap may comprise a lock to restrict the movement of the needle guard prior to removal of the cap. For example, the relative position of the slits and the protrusions may be locked out of alignment in the axial direction by elements of the cap when the cap is on a completed medicament delivery device, so that the protrusion and the slit cannot be aligned in the circumferential direction before the cap is removed.

This can help stop premature activation of a device, for example when a device is dropped before use (as retraction of the needle guard may trigger medicament delivery, and the needle guard cannot retract if the cap blocks the protrusions and slits from lining up. The lock could be a positive lock or a friction lock. In one example, the cap is rotationally restricted or rotationally locked relative to the shell, and a part of the cap, for example a second protrusion on the cap, limits the rotation of the medicament delivery member guard relative to the shell and the cap such that the protrusion and the slit cannot line up while the cap is attached to the medicament delivery device. This can stop the protrusion from entering the slit while the cap is on the medicament delivery device.

Various modifications to the embodiments described are possible and will occur to those skilled in the art without departing from the disclosure which is defined by the following claims.

The invention claimed is:

1. An assembly for a medicament delivery device, the assembly comprising:

a shell extending along an axis in an axial direction from a proximal end to a distal end: and a medicament delivery member guard moveably attached to the shell, the medicament delivery member guard extending in the axial direction from a proximal end to a distal end, wherein the shell comprising a slit extending in the axial direction and the medicament delivery member guard comprising a protrusion extending in the axial direction, and optionally the medicament delivery member guard comprising a slit extending in the axial direction and the shell comprising a protrusion extending in the axial direction, wherein the medicament delivery member guard is configured to move in the axial direction from a first axial position relative to the shell to a second axial position relative to the shell, such that in the first axial position the medicament delivery member guard is rotatable around the axis relative to the shell from a locked position in which the protrusion cannot enter the slit to an unlocked position in which the protrusion can enter the slit, such that in the second axial position rotation of the medicament delivery member guard around the axis relative to the shell is limited, and the protrusion is in the slit, and wherein the protrusion extends from the proximal end of the medicament delivery member guard.

2. The assembly of claim 1, wherein the protrusion extends from the medicament delivery member guard away from the axis in a radial direction.

3. The assembly of claim 1, wherein the slit extends through the shell in a radial direction relative to the axis.

4. The assembly of claim 1, wherein the slit extends only part of the way through the shell in a radial direction relative to the axis.

5. The assembly of claim 4, wherein the shell comprises an inner surface facing towards the axis, and the slit is in the inner surface of the shell.

6. The assembly of claim 1, wherein the slit extends in the axial direction from the proximal end of the shell.

7. The assembly of claim 1, wherein the medicament delivery member guard is inside the shell.

8. The assembly of claim 1, wherein the protrusion and the slit are adjacent to one another in the axial direction when the medicament delivery member guard is in the first axial position.

9. The assembly of claim 1, wherein the protrusion and the slit are spaced apart from one another in the axial direction when the medicament delivery member guard is in the first axial position.

10. The assembly of claim 1, wherein the medicament delivery member guard comprises a slit extending in the axial direction and the shell comprises a protrusion extending in the axial direction.

11. A medicament delivery device comprising the assembly of claim 1.

12. The medicament delivery device of claim 11, wherein the medicament delivery device comprises a cap, the cap comprising a lock to stop the protrusion from entering the slit while the cap is on the medicament delivery device.

13. The medicament delivery device of claim 11, wherein the medicament delivery device is an auto-injector.

* * * * *